United States Patent
Rigg et al.

[11] Patent Number: 5,785,960
[45] Date of Patent: Jul. 28, 1998

[54] METHOD AND SYSTEM FOR CUSTOMIZING DERMATOLOGICAL FOUNDATION PRODUCTS

[75] Inventors: Richard Tyson Rigg, Springfield Gardens, N.Y.; Jason Oliver Hendry, Cheshire; Madeline Demayo Flynn, Monroe, both of Conn.

[73] Assignee: Elizabeth Arden Co., Division of Conopco, Inc., New York, N.Y.

[21] Appl. No.: 820,516

[22] Filed: Mar. 19, 1997

[51] Int. Cl.⁶ .................................................. A61K 7/021
[52] U.S. Cl. .......................... 424/63; 364/400; 364/479; 364/479.02; 364/479.09; 366/160.1; 366/162.1
[58] Field of Search .............................. 424/63; 364/400, 364/479, 479.02, 479.09; 366/160.1, 162.1

[56] References Cited

U.S. PATENT DOCUMENTS 4,871,262  10/1989  Krauss et al. .......................... 366/160
5,622,692   4/1997  Rigg et al. ............................. 424/63

FOREIGN PATENT DOCUMENTS 41 10 299  3/1991  Germany.

*Primary Examiner*—Shelley A. Dodson
*Assistant Examiner*—Michael A. Williamson
*Attorney, Agent, or Firm*—Milton L. Honig

[57] ABSTRACT

A method and apparatus is provided for customizing a skin foundation product for a customer at a location remote from a central location where the product is prepared. The essential elements are that of a skin analyzer for reading skin properties, a telemodem means connectable to the device for transmitting the signal conveying information to a central monitoring location, a device at the central monitoring location which receives the reading and correlates same with an optimal formula and a formulation machine for preparing the facial foundation product from various cosmetic chemical compositions. The formulation machine receives instructions from the device on the optimal formula. This formula is then dosed and blended from a series of dispensers containing separate cosmetic chemical compositions into a receiving container. The container is then delivered to the customer at his remote site.

17 Claims, 1 Drawing Sheet

5,785,960

METHOD AND SYSTEM FOR CUSTOMIZING DERMATOLOGICAL FOUNDATION PRODUCTS

BACKGROUND OF THE INVENTION

1. Field of the Invention

The invention concerns a method and system for customizing skin foundation products at a central location away from a remote patient.

2. The Related Art

There are many reasons why consumers wish to purchase skin foundation products in private as opposed to the public spaces of retail conters. For example, patients seeking the medical advice of dermatologists for the treatment of skin defects often experience underlying emotional consequences. Frequently, once the defect, such as acne, burn tissue or eczema has been treated, the healthy skin may appear blotched, mottled, scarred or uneven in texture or color. Healthy skin may also exhibit rosacea or skin redness, birth marks or port wine stains regardless of the age or sex of the patient.

Skin discolorations have been generally left to the patient her/himself to address by seeking help at a cosmetics counter or aisle. Even if the customer gets past the embarrassment often associated with such public encounters, the selected product is often inappropriate for the skin type and need of the customer.

Cosmetic customers have been aided by a number of companies in the industry who have sought to provide a means for selecting the customer's optimal color shade. For example, Clinique and Clarion have installed computers at sales counters for use by the customer. Information on color shade, oiliness and other properties of a customer's skin are punched into the computer which then determines the company's most closely matching product.

Custom blending is also offered by two major companies, Prescriptives (division of Estee Lauder) and Visage (division of Revlon) who begin a sale by manually evaluating a subject's skin color. The salesperson then adjusts existing finished foundations so as to match the evaluated skin color. There are many disadvantages in manual blending. On many occasions there is a poor skin match, reproducibility is poor and extensive training is required of the salesperson. Additionally, the process is a cosmetic one which is embarrassing to patients unaccustomed to either buying cosmetics or who feel exposed at a public sales counter.

U.S. Pat. No. 4,871,262 (Krauss et al.) describes an automatic cosmetic dispensing system for blending selected additives into a cosmetic base. The system is intended for use at a retail establishment. A similar system is described in German Patent 41 10 299 C1 (Erdtmann), with the further element of a facial sensor. Although the aforementioned systems have advanced the cosmetic art, they are woefully lacking in addressing the needs of a person wishes to purchase a cosmetic skin product in a private setting.

Accordingly it is an object of the present invention to provide a method and system that will match the skin properties of a patient with a particular optimum formula in a private setting, such as a doctor's office, consumer's home, hospital clinic, costumer's office, etc.

Another object of the present invention is to provide a method and system for matching skin properties of a person in a remote location with an optimal cosmetic formula manufactured in a separate central location away from the point of skin measurement in a manner that is both accurate and repeatable.

A further object of the present invention is to provide a method and system for matching skin properties with an optimal cosmetic formula in a central location that requires only minimal training for the color scientist in selecting the proper product.

These and other objects of the present invention will become more readily apparent through consideration of the following summary, drawing and detailed description which follow.

SUMMARY OF THE INVENTION

A system for providing a customized skin foundation product to a customer at a location remote from a central location in which the skin foundation is prepared is described herein, the system comprising:

(a) a device for measuring a customer's skin coloration at a remote location and for generating signal conveying information of the measured natural skin coloration;

(b) telemodem means connectable to the device for transmitting the signal conveying information to a central monitoring location;

(c) a device located at the central monitoring location for receiving the signal conveying information from the telemodem means and converting the information into a set of operating instructions for an optimal skin foundation formula; and (d) a formulation machine for preparing the optimal skin foundation including:

(i) a mechanism for receiving the optimal skin foundation formula as the set of operating instructions, (ii) at least four dispensers, each containing one of at least four different chemical compositions, the chemical compositions being a red, yellow, black and white monochromatic composition, and (iii) a mechanism for activating dosing to a common dosing chamber of certain of the cosmetic chemical compositions and at certain concentrations as determined by the operating instructions to form a dosed formula;

(e) a mechanism for delivering the dosed formula into a container as a skin foundation product; and (f) means for transmitting the skin foundation product from the central monitoring system back to the remote location of the customer.

A method for customizing a skin foundation product to a customer at a location remote from a central monitoring location in which the product is prepared is also described. The method comprises the steps of:

(a) obtaining a reading of a customer's skin coloration and generating signal conveying information by applying a device for measuring coloration in proximity to the skin of the customer in a remote location;

(b) transmitting the signal conveying information by telemodem means to a device located at a central monitoring location;

(c) converting the signal conveying information to instructions for an optimal skin foundation in the device;

(d) transferring the instructions to a formulation machine for automatically preparing the optimal skin foundation;

(e) dosing together within the formulation machine a plurality of cosmetic chemical compositions including at least four different pigments selected from a red, yellow, black and white monochromatic compositions to form a dosed formula in accordance with the set of operating instructions;

(f) delivering into a container the dosed formula; and (g) transmitting the container from the central monitoring system back to the remote location of the customer.

Besides skin coloration, a variety of skin characteristics may be measured including moisturization, oiliness, texture, irritation sensitivity and markers of skin health such as radiance, skin damage, or age such as age spots.

The measuring device may be a spectrophotomer/colorimeter having a visible light source, such as light emitting diodes (LED), xenon-arc, tungsten-halogen, etc. in the wavelength range of 400–900 nm. The visible light source may form the sensor portion of the spectrophotomer/colorimeter. Both visible and infrared wavelength light may be utilized in connection with the sensor portion.

Advantageously, at least some of the cosmetic chemical compositions will be monochromatic emulsions. Most preferred is that the formulation machine contain at least four dispensers separately containing a red, yellow, black and white monochromatic composition. Either in separate dispensers or as ingredients of the monochromatic emulsions there may be included emollients, sunscreens, moisturizers, perfumes, solvents and wrinkling, skin-aging inhibitor, medication such as anti-acne, oil control, skin lightener, antiseptic and antibiotic ingredients.

An identification mark may be assigned to each customized facial foundation product. The marking may be labeled on the container as well as stored within the device and permanently identified with the customer. Especially useful as the marking is a bar code.

BRIEF DESCRIPTION OF THE DRAWING

Features and advantages of the present invention will more fully be appreciated by reference to the FIGURE which is the sole drawing and which diagrammatically illustrates the customization system.

DETAILED DESCRIPTION OF PREFERRED EMBODIMENTS

Figure 1:
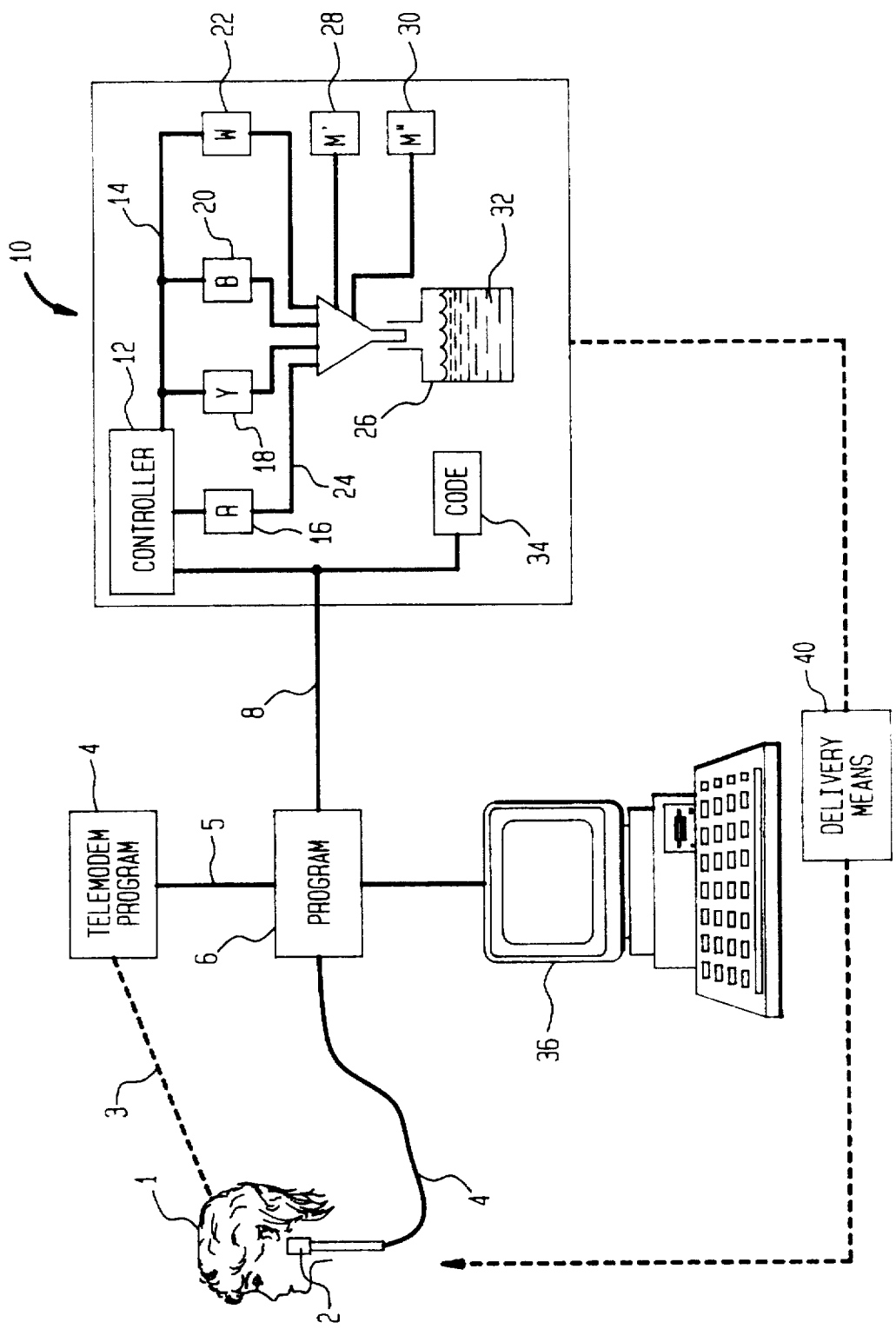

In accordance with the invention, the system has five essential modules. These modules include an electronic skin analyzer for skin measurements at a remote location, telemodem means, a device located at a central location to translate the skin measurements to instructions for optimal skin formula, a machine for dispensing-mixing of an optimal skin formula and means for transmitting the formula from the central location back to the customer's remote location. These modules will be capable of electronically communicating with one another.

The skin analyzing module is preferably a hand-held spectrophotometer/colorimeter operating with at least one visible light source such as LED, xenon-arc, tungsten-halogen, etc. Suitable skin analyzers are commercially available from Minolta Camera Co. Ltd, Japan (Minolta Spectrophotometer/colorimeter CM-2002) and from Colortec Associates (diffused illumination/diffused viewing) Spectrophometer, such as X-Rite Spectrophotometer The module is preferable portable so that a customer's skin coloration may be measured at a location remote to a central monitoring location. Such remote locations include a physician's office, a customer's home, hospital, clinic or workplace.

The next component of the system is a telemodem means which is used to transmit the information from the skin analyzing module at the customer's remote location to a device at a central monitoring site. The telemodem means may utilize a telephone linkage to transmit the information, fax, postal service, LAB display or any other conventional means known in the art.

The next essential component of the apparatus is that of a device which may be a module separate from or housed commonly within the skin analyzing unit. The device will translate the signal conveying information into instructions for an optional skin formula data for the foundation product.

Another essential module of the apparatus is that of a formulation machine. The machine will include a series of dispensers, each containing a different cosmetic chemical composition. Each of the dispensers will be connected into a common dosing chamber through respective tubing. An electronic control board will also be part of the machine. This board will receive electronic instructions from the programmable device as to the optimal formula necessary to be dispensed. Servomechanical activators will be present within the machine to operate discharge valves for the respective dispensers. In accordance with the selected optimal formula, the requisite valves will be opened and the length of opening time will be regulated pursuant to the required quantity of any particular cosmetic chemical composition to be dispensed. Advantageously, the dosing chamber will be in the form of a dispensing container provided directly to the customer and serving as the product's package. The package may be disposable or multiple use. The machine will also be capable of adjusting sample sizes of the dosed-mixed optimal formula.

A marking mechanism may also be associated with the apparatus, preferably housed together with the formulation machine. The marking mechanism may utilize any numerical scheme, e.g. a customer's name, Social Security number, and/or other personalized identification, for connection with the optimal cosmetic product selected through the skin measuring process. Advantageously, the marking will be in the form of a bar code symbol.

Sometimes a customer may wish to alter the selected optimal formula. For such purpose, a further module is provided wherein a customer's preference can be entered to the program through a keyboard, or fax information which can be keyed in a central location.

A highly diagrammatic representation of the apparatus is provided in the FIGURE. Therein is shown a customer 1 whose facial skin is being measured by a portable skin analyzer 2. The resultant reading or signal is transferred electronically via line 3 to a telemodem means 4 which, in turn, transmits the signal to a device 6 via a line 5. The skin readings are translated in the device 6 to instructions for an optimal formula. The optimal formula is then identified and that information is transferred via line 8 to a formulation machine 10 where it is directed to a controller unit 12. Servomechanical devices 14 are operated in conjunction with the information on the optimal formula.

When a particular facial foundation is required, an optimal color shade is delivered by combining a mixture of monochromatic compositions each of which is dosed from a respective dispenser. These dispensers contain a cosmetic chemical composition exhibiting one of four monochromatic colors, i.e. Red 16, Yellow 18, Black 20 and White 22. These colors will typically be achieved by incorporation of a respective iron oxide pigment (e.g. red iron oxide, yellow iron oxide or black iron oxide). White can be obtained from titanium dioxide.

The servomechanical device 14 operates a series of valves associated with each of the dispensers to deliver the proper amount of each monochromatic colored composition. Delivery is through a system of tubing 24 which leads to a common dosing chamber 26. The dosing chamber is shown as an empty cosmetic bottle. A moisturizing composition M' or modifying finish M" may also be provided from separate dispensers 28, 30 into the dosing chamber 26. The customized facial foundation product 32 is then packaged for delivery back to the customer 1 at his/her remote location via any conventional delivery means 40 such as mail overnight carrier, etc. Any customer changes which may be required may be again transmitted from the customer 1 via the telemodem means 4 to the device 6 for alteration of the determined optimum formula by instructions manually transmitted into the keyboard terminal 36. A final facial foundation product is then dispensed, mixed and packaged. Affixed to the package 32 will be a bar code printed through coder 34.

The method for customizing the cosmetic product is as follows. A region on a customer's face will be cleaned preparatory to a reading. The spectrophotomer/colorimeter will then be placed in proximity to the cleaned facial area. Visible light emitted in the 400–900 nm range by the device will be reflected off the skin surface and the reflected wavelength measured. A total of three skin readings along the neck/jaw line region will be taken. Total time for the reading will be approximately 30 seconds.

The collected wavelength information will then be transmitted via a telemodem means 4 from the customer's remote location to the device. The device correlates the reading from the device with the optimal formula. Information on this formula will then be transferred to the controller portion of a formulation machine. This information will then be translated into operating instructions to the dispensing unit. The selected cosmetic chemical compositions and their amounts will then be dosed to a dispensing container. A bar code containing shade and formula information may be affixed to the package. Information on the purchased cosmetic formula will also be stored in a central computer. At any subsequent time, the customer may request additional samples. Based on the bar code information, the exact same optimal formula can be prepared as a refill.

The method of this invention allows preparation of a relatively infinite number of different cosmetic formulations, e.g. color shades, to allow for enormous variations. The transportable aspect most importantly provides a customer with a much needed foundation product without the embarrassment or inconvenience of going to a retail location. On the commercial aspects, there will be no need to maintain in inventory a large number of different shades of color cosmetic, many of which will never be sold. Moreover, the method promises that a specific color shade or formulation would not be discontinued for lack of sales.

The foregoing description illustrates selected embodiments of the present invention and in light thereof variations and modifications will be suggested to one skilled in the art, all of which are within the spirit and purview of this invention.

What is claimed is:

1. A method for customizing a skin foundation product to a customer at a location remote from a central monitoring location in which the product is prepared is also described. The method comprises the steps of:
   (a) obtaining a reading of a customer's skin coloration and generating signal conveying information by applying a device for measuring coloration in proximity to the skin of the customer in a remote location;
   (b) transmitting the signal conveying information by telemodem means to a device located at a central monitoring location;
   (c) converting the signal conveying information in the device to a set of operating instructions for an optimal skin foundation;
   (d) transferring the set of operating instructions to a formulation machine for automatically preparing the optimal skin foundation;
   (e) dosing together within the formulation machine a plurality of cosmetic chemical compositions including at least four different pigments selected from a red, yellow, black and white monochromatic compositions to form a dosed formula in accordance with the set of operating instructions;
   (f) delivering into a container the dosed formula; and
   (g) transmitting the container from the central monitoring system back to the remote location of the customer.

2. A method according to claim 1 wherein the means for measuring coloration can also measure at least one skin characteristic selected from the group consisting of a customer's skin moisturization, oiliness, texture, irritation sensitivity, skin color, skin tone, aging markers and combinations thereof.

3. A method according to claim 1 wherein the means for measuring is a spectrophotometer/colorimeter.

4. A method according to claim 3 wherein the spectrophotometer/colorimeter is formed with at least one visible light source having a wavelength in the range of 400–900 nm.

5. A method according to claim 3 wherein the spectrophotometer/colorimeter measures visible wavelength light which interacts with the skin.

6. A method according to claim 3 wherein the spectrophotometer/colorimeter measures infrared wavelength light which interacts with the skin.

7. A method according to claim 1 wherein the monochromatic compositions or other non-monochromatic cosmetic chemical compositions include ingredients that are selected from the group consisting of emollients, sun-screens, moisturizers, perfumes, solvents, wrinkling and skin-aging inhibitors and medicines, oil control agents, anti-acne agents, skin whitening actives, antiseptics, antibiotics, anti-inflammatory agents and combinations thereof.

8. A method according to claim 1 further comprising the step of a customer inputting a modification to alter the selected optimal formula.

9. A method according to claim 1 further comprising the step of assigning an identification mark to each customized facial foundation product, labeling on the container the mark, and storing the identification to permanently identify the customized facial foundation product with the customer.

10. A method according to claim 9 wherein the marking is in the form of a bar code.

11. An apparatus for providing a customized skin foundation product to a customer at a location remote from a central location in which the skin foundation is prepared is described herein, the system comprising:
   (a) a device for measuring a customer's skin coloration at a remote location and for generating signal conveying information of the measured skin coloration;
   (b) telemodem means connectable to the device for transmitting the signal conveying information to a central monitoring location;
   (c) a device located at the central monitoring location for receiving the signal conveying information from the modem means and converting the information into a set of operating instructions for an optimal skin foundation formula; and (d) a formulation machine for preparing the optimal skin foundation including:
  (i) a mechanism for receiving the optimal skin foundation formula as the set of operating instructions,
  (ii) at least four dispensers, each containing one of at least four different chemical compositions, the chemical compositions being a red, yellow, black and white monochromatic composition, and
  (iii) a mechanism for activating dosing to a common dosing chamber of certain of the cosmetic chemical compositions and at certain concentrations as determined by the operating instructions to form a dosed formula;

(e) a mechanism for delivering the dosed formula into a container as a skin foundation product; and (f) means for transmitting the skin foundation product from the central monitoring system back to the remote location of the customer.

12. The apparatus according to claim 11 wherein the means for measuring coloration can also measure at least one skin characteristic selected from the group consisting of the customer's skin moisturization, oiliness, texture, irritation sensitivity, skin color, skin tone, aging markers and combinations thereof.

13. The apparatus according to claim 11 wherein the means for measuring is a spectrophotometer/colorimeter.

14. The apparatus according to claim 13 wherein the spectrophotometer is formed with at least one visible light source having a wavelength in the range of 400–900 nm.

15. The apparatus according to claim 11 further comprising a means for the customer to input a modification to the signal generated by the measuring means.

16. The apparatus according to claim 11 further comprising a means to mark with an identification mark each customized facial foundation product.

17. The apparatus according to claim 16 wherein the identification mark is a bar code.

* * * * *